US009445984B2

(12) United States Patent
Mateu et al.

(10) Patent No.: US 9,445,984 B2
(45) Date of Patent: Sep. 20, 2016

(54) TWO-PART COSMETIC PRODUCT WITH SWELLING EFFECT TO BIOLOGICAL SURFACES

(75) Inventors: Juan R. Mateu, Oak Ridge, NJ (US); Salvatore J. Barone, Staten Island, NY (US); Ralph Anthony Macchio, Sparta, NJ (US)

(73) Assignee: Coty Germany GmbH, Mainz (DE)

( * ) Notice: Subject to any disclaimer, the term of this patent is extended or adjusted under 35 U.S.C. 154(b) by 292 days.

(21) Appl. No.: 12/866,971

(22) PCT Filed: Jan. 22, 2009

(86) PCT No.: PCT/EP2009/050729
§ 371 (c)(1),
(2), (4) Date: Oct. 5, 2010

(87) PCT Pub. No.: WO2009/100974
PCT Pub. Date: Aug. 20, 2009

(65) Prior Publication Data
US 2011/0027210 A1 Feb. 3, 2011

(30) Foreign Application Priority Data

Feb. 12, 2008 (EP) .................................. 08151337
Aug. 25, 2008 (EP) .................................. 08162917

(51) Int. Cl.
*A61K 8/891* (2006.01)
*A61Q 1/12* (2006.01)
*A61Q 1/10* (2006.01)
*A61Q 1/06* (2006.01)
*A61Q 1/04* (2006.01)

(52) U.S. Cl.
CPC ................ *A61K 8/891* (2013.01); *A61Q 1/04* (2013.01); *A61Q 1/06* (2013.01); *A61Q 1/10* (2013.01); *A61Q 1/12* (2013.01); *A61K 2800/88* (2013.01)

(58) Field of Classification Search
CPC .......... A61K 8/891; A61Q 1/12; A61Q 1/10; A61Q 1/06; A61Q 1/04
See application file for complete search history.

(56) References Cited

U.S. PATENT DOCUMENTS

| | | | |
|---|---|---|---|
| 6,331,604 B1 | 12/2001 | Wang et al. | |
| 6,682,749 B1 * | 1/2004 | Potechin et al. | .............. 424/401 |
| 2005/0266064 A1 | 12/2005 | McCarthy | |
| 2007/0142575 A1 | 6/2007 | Zheng et al. | |

FOREIGN PATENT DOCUMENTS

| | | | | |
|---|---|---|---|---|
| EP | 1859779 | * 11/2007 | ............... | A61K 8/37 |
| WO | 2009/043898 | 4/2009 | | |

OTHER PUBLICATIONS

Eitrich et al, EP 1859779—Machine Translation, Nov. 2007, European Patent Office, pp. 1-28.*
Nanavati et al, A preliminary investigation of the interaction of a quat with silicones and its conditioning benefits on hair, 1994, J. Soc. Cosmet. Chem., 45, pp. 135-148.*

* cited by examiner

*Primary Examiner* — Trevor Love
(74) *Attorney, Agent, or Firm* — Schwegman Lundberg & Woessner, P.A.

(57) ABSTRACT

The invention relates to a two part cosmetic composition for application to a biological surface to impart a swelling effect comprising a siloxane polymer with at least two hydroxy-functionalized terminal groups or hydroxy-functionalized side chains and/or a polyol with at least two hydroxyl groups, a hydrosiloxane with at least two Si—H units and a catalyst, wherein in one part of the composition the siloxan polymer and/or the polyol and the catalyst or the hydrosiloxane are contained and in the other part of the composition the hydrosiloxane or the catalyst are contained and wherein said catalyst catalyzes in-situ cross-linking of the siloxane polymer or polyol and the hydrosiloxane by dehydrogenative coupling to form a foamed elastomeric transfer resistant film after combination of the two parts.

14 Claims, No Drawings

TWO-PART COSMETIC PRODUCT WITH SWELLING EFFECT TO BIOLOGICAL SURFACES

The present invention relates to a two-part cosmetic composition that imparts a filling and/or swelling effect to biological surfaces, preferably to human skin. The invention uses a dehydrogenative coupling reaction to expand and swell a film former contained in the two-part cosmetic composition with the in situ generated hydrogen when the dehydrogenative coupling takes place. The resulting film has also a high transfer resistance.

For many cosmetic formulations it is desirable to provide volumizing effects to the human skin. In order to maintain a juvenescent appearance masking and smoothing of wrinkles, microreliefs, pores and other defects of the contour of the skin is a permanent requirement for make-up formulations to result in a modified visual perception. Especially lips have to be smooth and voluminous in order to give women a "pouty" appearance. Thus, cosmetic care compositions are required which are able to provide both colouring and volumizing effects.

Permanent lip enhancement is based on surgery methods including implants or injections of collagens, silicones, fats or hyaluronic acid derivatives. All invasive methods comprise great disadvantages, for instance the risk of infection or the formation of unaesthetic scars.

Most of the non-invasive methods are based on the application of active substances to the skin in order to increase the natural humidity. Unfortunately, these effects are usually short lived. Further, unpleasant feelings can occur after the application. For example after the application of collagens or hyaluronic acids lips seem to be coated with a thin film.

Application of camphor, menthol products or cinnamon oil is used to irritate the mucosa and to cause dilation of the adjacent capillaries. This induces an increase in blood circulation and swells the lips, because numerous blood vessels are located beneath the thin skin of the lips. However, these blood vessels also carry away from the lip tissue active compounds so that effectiveness is reduced and increases in volume can be short lived.

Thus, US 20050266064 discloses an extended release delivery system which provides sufficient storage and release in order to permit automatic reapplication of active substances to the lips.

Another possibility is the use of conventional makeup, which makes it possible to mimic the effects by acting especially on optical phenomena that consist in creating localized gloss in well defined regions of the lips or by superposing two type of gloss in order to create an optical illusion and thus create a sensation of volume.

Artificial expanding compositions for the application to hair, eyelashes or eyebrows are known in the state of the art. For example, EP 07 117 999.8 discloses post-application expanding compositions that use in situ generated $CO_2$ to foam the surfactant components of the composition. A film-forming component of the composition is used to entrap at least a portion of the foam lattice and, when set, fix the composition in an expanded state.

It would be desirable to have a cosmetic formulation with a long lasting volumizing effect to human skin, especially to lips, which is based on an artificial volumetric effect and which provides after expansion a clear, smooth, flexible and durable film on the skin which feels natural and comfortable and satisfies the aesthetic requirements of the consumers.

It is an object of the present invention to provide a two-part cosmetic product based on silicone polymers for imparting swelling effects to human skin, in particular to the lips.

It is another object of the present invention to provide a two-part cosmetic product in kit form, the kit comprising in different chambers of a single two chambered container or in two separate containers the different parts of the composition, wherein both parts being applied sequentially to the skin and/or to the lips.

It is still another object of the present invention to provide a method for imparting swelling effects to human skin, in particular lips, by applying the two-part cosmetic product of the invention.

The present invention provides a two part cosmetic composition for application to a biological surface, in particular human skin, to impart a swelling effect comprising a siloxane polymer with at least two hydroxy-functionalized terminal groups or hydroxy-functionalized side chains and/or a polyol with at least two hydroxyl groups, a hydrosiloxane with at least two Si—H units and a catalyst, wherein in one part of the composition the siloxane polymer and/or the polyol and the catalyst or the hydrosiloxane are contained and in the other part of the composition the hydrosiloxane or the catalyst are contained and wherein said catalyst catalyzes in-situ cross-linking of the siloxane polymer or polyol and the hydrosiloxane by dehydrogenative coupling to form a foamed elastomeric transfer resistant film after combination of the two parts.

That means, the cosmetic product of the invention has two compositional parts for sequential application to human skin. In a first embodiment one part of the composition comprises a siloxane polymer with at least two hydroxy-functionalized terminal groups or hydroxy-functionalized side chains. Suitable siloxane polymers are for instance dimethiconol, a dimethiconol copolymer and/or a derivative thereof, in particular dimethiconol solution in cyclomethicone.

In another embodiment a hydroxy-functionalized silicate resin can be used as the siloxane polymer. The silicate resin is for example a silicone silicate copolymer, preferably a dimethiconol silicone silicate copolymer and most preferred trimethylsiloxysilicate.

In another embodiment a polyol with at least two hydroxyl groups can be comprised in the siloxane polymer containing part of the composition as well. Thereby, the expression polyol is used for all organic substances with at least two hydroxyl groups. In particular, alcohols are preferred, but substances which contain further functional groups, such as ether, ester or anhydride groups are also included. Suitable polyols are glycerine, diglycerine and/or derivatives thereof.

In a preferred embodiment of the invention the polyol is a copolymerized hydroxyl functionalized vegetable or synthetic oil or a mixture thereof. Suitable vegetable oils according to the invention are for instance olive oil, castor oil, sunflower oil, linseed oil, tall oil, soybean oil, colza oil, fish oil, cottonseed oil, palm oil, palm kernel oil, coconut oil, canola oil, flaxseed oil, heigh oleic canola oil, safflower oil and every other known saturated and unsaturated vegetable oil. Preferred synthetic oils are paraffin oils, such as isoparaffin, ozokerite or ceresine and silicone oils, such as dimethicone or cyclomethicone.

Preferably the copolymerized hydroxyl functionalized vegetable and/or synthetic oils are copolymerised with an ester, a diester, a triester, urethanes and/or dimer diols. Surprisingly it was found that the copolymerized hydroxyl functionalized vegetable and/or synthetic oils can be used as a polyol according to the invention. If the hydroxyl functionalized vegetable and/or synthetic oils are used directly the reactants do not react properly and a weak paste is achieved. Only a slight increase of the viscosity is observed. In contrast reacting the copolymerized hydroxyl functionalized vegetable and/or synthetic oils together with a hydrosiloxane a very strong gel is achieved. The resulting gels show a foam-paste-solid/rubbery texture.

Every known vegetable and/or synthetic oil can be used to form the copolymers according to the invention. Suitably copolymers are diisostearyl polyglyceryl-3-dimer dilinoleate (Schercemol™ PDD), triisostearyl polyglyceryl-3-dimer dilinoleate (Schercemol™ TPID), hydrogenated castor oil dimer dilinoleate (Risocast® DA-H or Risocast® DA-L), hydrogenated castor oil isopropyl dimer dilinoleate, hydrogenated castor oil/sebacic acid copolymer (Crodabond CSA), castor oil/3-isocyanateomethyl-3,5,5-trimethylcyclohexyl isocyanate copolymer (Castor Oil/IPDI Copolymer, Polyderm® PPI-CO), castor oil/dimer diol copolymer, or castor oil/isocetyl alcohol copolymer or a mixture thereof.

According to the invention the use of compounds with more than two hydroxyl groups is preferred. The higher number of reactive sites, i.e. the higher number of hydroxyl groups, increases the reaction rate of the film forming reaction and allows the reduction of the catalysts. Further the gel strength of the cross-linked gel is increased. Thus, the number of functional groups in the reactive compounds is varied in order to improve the solubility of the resulting gel.

In a preferred embodiment a copolymer of a hydroxyl functionalized vegetable and/or synthetic oil with isocetyl alcohol and/or dimer diols is used. These copolymers show an improved reaction. Only after contact of the films the reaction starts so that no further mixing is needed. Thus, the foaming of the gel and the resulting volume effect are further enhanced.

In another embodiment the polyol, preferably the copolimerized hydroxyl functionalized vegetable and/or synthetic oils, are contained instead of the siloxane polymer in one part of the cosmetic composition. This is highly advantageous because the copolymerized hydroxyl functionalized vegetable and/or synthetic oils can be used directly and no further solvents, such as silicone oils are needed. Further, the resulting gel is a silicone/organic compound which shows a better compatibility with human skin. Thus, these cosmetic compositions are also applicable to human skin which is very sensitive and/or shows allergic reactions to silicone compounds, including silicone solvents.

The siloxane polymer and/or the polyol containing part of the composition comprises about 1 to about 60 weight % of the polymer and/or the polyol. In particular, at about 10 to about 50 weight %, more preferred at about 20 to about 30 weight % and most preferred about 25 weight % of the siloxane polymer and/or the polyol are contained. All weight % are based on the total weight of the siloxane polymer and/or polyol containing part of the composition.

According to the invention a mixture of one, two or more hydroxy-functionalized siloxane polymers or one, two or more polyols or a mixture thereof can be used in the dehydrogenative-coupling reaction of the invention. In a preferred embodiment a siloxane polymer and a polyol, in particular a copolymerized hydroxyl functionalized vegetable and/or synthetic oil are used as mixture. A suitable ratio of the two components is from 1:5 to 5:1 siloxane polymer to polyol. Most preferred the siloxane polymer and the polyol are mixed in equal amounts, i. e. in a ratio of 1:1.

The siloxane polymer and/or polyol containing part of the composition further comprises either a hydrosiloxane with at least two Si—H units or a catalyst. According to the invention the hydrosiloxane and the catalyst are always contained in different parts of the cosmetic composition. The combination of both components in one part is not preferred, because after mixing of both components the preferred gelling of the silicone polymer does not occur. If one part of the composition comprises the hydrosiloxane, the catalyst has to be contained in the other part of the composition and vice versa.

As a hydrosiloxane polymethylhydrosiloxane is preferred, but according to the invention other hydrosiloxanes suitable for cosmetic compositions can also be used. In a preferred embodiment the hydrosiloxane is contained in the siloxane polymer and/or polyol containing part of the composition.

The hydrosiloxane is contained at about 0.1 to about 50 weight %, preferably at about 1 to about 30 weight %, more preferred at about 10 to about 25 weight and most preferred about 15 weight %. All weight % are based on the total weight of the hydrosiloxane containing part of the composition.

In a preferred embodiment the molecular weight of the reactants is used to determine the physical properties of the cosmetic composition according to the invention. A higher molecular weight increases the water resistance of the cosmetic composition and the adhesion and/or cohesion to the human skin. Furthermore a better skin feeling and a brighter shine of the cosmetic composition are obtained. More preferred compounds with a higher molecular weight of the non-hydroxyl part of the compounds are used. The higher the molecular weight in the non-hydroxyl part of the reactants the greater the flexibility of the resulting gel structure.

In another preferred embodiment the catalyst is contained in the siloxane polymer and/or polyol containing part of the composition and the other part of the composition comprises the hydrosiloxane.

As a catalyst every catalyst is preferred which is able to catalyse a dehydrogenative coupling reaction. In particular, a metal selected from the transition metals of the VIII B group of the chemistry's periodic table, preferably platinum or palladium, are preferred. The most preferred catalyst according to the invention is platinum-divinyl tetramethyl-disiloxane complex.

The catalyst is contained at about 0.001 to about 3 weight %, in particular at about 0.01 to about 2 weight %, more preferred at about 0.1 to about 1.5 weight % and most preferred about 1 weight %. All weight % are based on the total weight of the catalyst containing part of the composition.

In another preferred embodiment the cosmetic composition further comprises cosmetically acceptable auxiliary substances. The cosmetically acceptable auxiliary substances can be contained in one part or in both parts of the composition. Suitable cosmetically acceptable auxiliary substances according to the invention are colorants, powders, solvents, fillers, preservatives, actives, natural and synthetic oils and/or waxes, esters, or emulsifiers or mixtures thereof.

As a colorant any cosmetically acceptable pigment or natural or synthetic organic or inorganic dye or mixtures thereof can be used according to the invention. According to the invention pigments are white or coloured, mineral or organic particles that are insoluble in the solvent and which are intended to colour and/or opacify the composition.

Examples for mineral pigments which can be used according to the invention are made of titanium oxide, titanium dioxide, zirconium oxide or cerium oxide, and also zinc oxide, iron (II; III) oxide, chromium oxide or bismuth oxychloride. Further, ferric blue, manganese violet, copper powder and bronze powder can be used. As organic pigments the use of carbon black, and barium, strontium, calcium (D & C Red No. 7) and aluminium lakes is preferred. Dyes may be soluble in water or organic solvents. Preferred dyes are for example Red 7 Ca. Lake, Sudan red, D & C Red 17, D & C Green 6, beta-carotene, soybean oil, Sudan brown, D & C Yellow 11, D & C Violet 2, D & C Orange 5, quinoline yellow, annatto and beetroot juice.

In a preferred embodiment nacres or goniochromatic pigments, for example multilayer interference pigments, and/or reflective pigments may be included in the two-part cosmetic composition. As nacres coated mica can be used according to the invention. The mica can be coated with titanium oxide, iron oxide, natural pigments or bismuth oxychloride.

The colorant is present in an amount sufficient to impart a colour to the human skin on which it is applied. The composition of the invention includes at about 0.1 to about 30 weight % colorants, preferably at about 0.2 to about 25 weight %, more preferred at about 1 to about 20 weight % and most preferred at about 5 to about 15 weight %. All weight % are based on the total weight of the colour containing part of the composition.

In another preferred embodiment the pigments of the colorants are bonded physically or chemically to the reactants. According to the invention reactants are the three essential components which are needed for the dehydrogenative coupling (the siloxane polymer and/or the polyol, the hydrosiloxane and the catalyst).

Bonded pigments are classified as treated pigments.

In a preferred embodiment the pigments are treated with dimethiconol or dimethiconol copolymers. The dimethiconol copolymer can be blended further with polymethylhydrosiloxane. Alternatively, glycerine and glycerine derivatives can be used for pigment treatment.

In another preferred embodiment the two part cosmetic composition further comprises powders and/or mineral or synthetic particles of any form. As mineral particles mica, talc, silica and/or kaolin are preferred. Synthetic particles can be made of acrylic acid polymers, such as polymethylmetacrylate (PMMA), polyamide, polyethylene or polyurethane or mixtures thereof.

Powders are contained at about 1 to about 40 weight %, preferably, at about 10 to about 30 weight %, most preferred at about 15 to about 20 weight %. All weight % are based on the total weight of the powder containing part of the composition.

In another preferred embodiment treated powders are used which are bonded physically or chemically to the reactants. In a preferred embodiment the treated powders are used instead of the treated pigments. In another preferred embodiment treated pigments and treated powders are used together.

As fillers any cosmetically acceptable filler known to a person skilled in the art can be used according to the invention.

In another preferred embodiment the catalysts are treated with inorganic or organic pigments. Preferably the catalysts are treated with the colorants, powders and/or fillers according to the invention. Preferably organic dyes, iron oxides, mica and/or talc are used for treatment of the catalysts.

According to the invention any cosmetically acceptable hydrocarbon or silicone can be used as a solvent. As hydrocarbons alkanes or isoalkanes are preferred, in particular isoparaffins, for instance isododecane, isodecane and isohexadecane or isohexyl neopentanoate or mixtures thereof. Isododecane is preferred according to the invention. As silicone dimethicone and derivatives thereof, such as dimethiconol, amodimethicone, cyclomethicones, phenyl trimethicone, dimethicone copolyol, stearyl dimethicone, cetyl dimethicone or mixtures thereof are preferred. According to the invention it is especially preferred to use dimethiconol in cyclomethicone silicone oil, preferably DC 1501 (Dow Corning) or cyclomethicone. But also other cosmetically acceptable solvents like, esters or vegetable oils may be applied. The amount of the solvent is calculated separately in each composition in order to reach 100 weight %.

Suitable preservatives are for instance parabens, phenoxyethanol, caprylyl glycol or any typical preservative or mixtures thereof used in the personal care/cosmetic industry.

In another preferred embodiment further cosmetically active ingredients, called actives, can be contained in the two part cosmetic composition. In particular, the group of the actives comprises vitamins, provitamins, coenzymes, antioxidants, trace elements, hyaluronic acid, peptides, or proteins or mixtures thereof. As proteins enzymes and/or proteins of the extracellular matrix are preferred.

Natural and synthetic oils which are used in the personal care/cosmetic industry are suitable for the two-part cosmetic composition according to the invention. In particular, hydrogenated oils, for instance jojoba oil, avocado oil, borage oil, thistle oil, groundnut oil, St. John's wort oil, coconut oil, sweet almond oil, evening primrose oil, ricinus oil, sesame oil, sun flower oil or wheat germ oil or mixtures thereof are preferred.

The waxes that may be used in the two-part cosmetic composition of the invention are cosmetically acceptable compounds that are solid at room temperature, which are intended to structure the composition in particular in stick form. Suitable compounds may be hydrocarbon-based waxes and/or silicone waxes, in particular of plant, mineral, animal and/or synthetic origin. They may have a melting point of greater than 40° C. and better still greater than 45° C.

All waxes which are generally used in personal care/cosmetic industry can be used. Suitable natural waxes are for instance beeswax, preferably PEG8-Beeswax, carnauba wax, candelilla wax, ouricoury wax, Japan wax, cork fibre wax, sugarcane wax, rice wax, montan wax, paraffin, microcrystalline wax or ceresin or mixtures thereof. Suitable synthetic waxes are for instance polyethylene or ozokerite, mineral waxes or emulsifying waxes or alternatively fatty acid esters, for instance octacosanyl stearate or glycerides that are solid until the required temperature or mixtures thereof. The waxes are contained at about 1 to about 20 weight %, preferably at about 5 to about 15 weight %, most preferred at about 10 weight % based on the total weight of the wax containing part of the composition.

As esters any cosmetically acceptable ester can be comprised as an auxiliary substance. Esters which are known for their antiseptic properties and which are conventionally used in this respect in compositions intended to be administered to man or animals as pharmaceutical, nutritional and cosmetic compositions are preferred. The presence of these compounds ensures stability over time for the corresponding compositions.

As emulsifier every cosmetically acceptable emulsifier known to the person skilled in the art can be used according to the invention. Suitable emulsifiers according to the invention are Glyceryl Stearate, PEG-100 Stearate, such as Arlacel® 165V or stearyl alcohol or mixtures thereof.

In a preferred embodiment one part of the composition comprises the hydroxy-functionalized siloxane polymer and/or polyol, colorants, powders, waxes, solvents and the catalyst. All components are contained in the amounts which are mentioned above.

According to the invention the other part of the composition comprises the hydrosiloxane so that all three reactants which are essential for the dehydrogenative coupling reaction are contained in the two parts of the composition. In a preferred embodiment the other part of the composition comprises the hydrosiloxane and a solvent. The amount of the hydrosiloxane is given above. Thus, the solvent is contained at about 50 to about 99.9 weight %, preferably at about 70 to about 99 weight %, more preferred at about 75 to about 90 weight % and most preferred about 85 weight %. All weight % are based on the total weight of that part of the composition.

In another preferred embodiment one part of the composition comprises the hydroxy-functionalized siloxane polymer and/or polyol, colorants, powders, waxes, solvents and the hydrosiloxane. All components are contained in the amounts which are mentioned above.

According to the invention the other part of the composition comprises at least the catalyst. In particular the other part of the composition comprises the catalyst and a solvent. The amount of the catalyst is given above. Thus, the solvent is contained at about 97 to about 99.999 weight %, preferably at about 98 to about 99.99 weight %, more preferred at about 98.5 to about 99.9 weight % and most preferred at about 99 weight %. All weight % are based on the total weight of that part of the composition.

In another preferred embodiment the other part of the composition comprises the catalyst, preservatives and a solvent. The preservatives are contained at about 1 to about 4 weight %, preferably at about 2 to about 3 weight %. All weight % are based on the total weight of that part of the composition. The amount of the solvent is calculated in order to reach 100 weight %.

In another preferred embodiment one part of the composition comprises treated pigments and/or treated powders, preservatives and solvents. Treated pigments are contained at about 0.1 to about 30 weight %, preferably at about 0.2 to about 25 weight %, more preferred at about 1 to about 20 weight % and most preferred at about 5 to about 15 weight %. Preservatives are contained at about 1 to about 4 weight %, preferably at about 2 to about 3 weight %. All weight % are based on the total weight of that part of the composition. The amount of the solvent is calculated in order to reach 100 weight %.

In a preferred embodiment one part of the composition comprises treated pigments and/or powders, wherein the colorants and/or powders are bonded to the hydroxy-functionalized siloxane polymer and/or the polyol and the catalyst. Thus, the other part of the composition comprises the at least the hydrosiloxane according to the invention.

In another preferred embodiment one part of the composition comprises treated pigments and/or powders, wherein the colorants and/or powders are bonded to the hydroxy-functionalized siloxane polymer and/or the polyol and the hydrosiloxane. Thus, the other part of the composition comprises at least the catalyst according to the invention.

In another preferred embodiment one part of the composition comprises treated pigments and/or powders, wherein the colorants and/or powders are bonded to the hydrosiloxane. According to the invention the other part of the composition comprises at least the hydroxy-functionalized siloxane polymer and/or the polyol and the catalyst.

In the other part of the composition the hydroxy-functionalized siloxane polymer and/or the polyol are contained at about 0.2 to about 40 weight %, preferably at about 1 to about 30 weight % and most preferred at about 10 to about 25 weight %. All weight % are based on the total weight of that part of the composition. The amount of the solvent is calculated in order to reach 100 weight %.

After combining all essential reactants, i.e. the hydroxy-functionalized siloxane polymer and/or the polyol, the hydrosiloxane and the catalyst, a dehydrogenative coupling takes place. Thereby, the silicones are cured and a soft to rigid film arises. During the dehydrogenative coupling hydrogen gas is released. The escaping hydrogen induces a foaming of the silicone polymers which results in an increase in volume. The cured silicone film is strong enough to retain the foam and to conserve the volumetric effect. The resulting film also imparts a high transfer resistance. Once the film is set it resists transfer for instance by hydrocarbon solvents, water, oils, silicones, esters, organic compounds, soap.

The preparation of the two-part cosmetic composition is the same as for conventional product forms.

For the preparation of one part of the composition the siloxane polymer and/or the polyol, the wax(es) and the preservative(s) are heated to about the melting temperature of the wax(es) and mixed until they are homogeneous. Then the colorant, the powder and the hydrosiloxane are added under stirring. For the other part of the composition the catalyst is solved in the solvent under stirring by room temperature.

It is important, that the platinum catalyst is not heated over 50° C. This would reduce the catalytic function. However, there are embodiments of the invention, wherein one part of the composition has to be heated over 50° C. in order to melt wax(es) with a high melting point, for instance for the production of lipsticks. In that case the catalyst has to be comprised in the other part of the composition which is not heated.

The texture of the two part cosmetic composition comprises solids, pressed powders, crèmes, gels, lotions or liquids.

In a preferred embodiment the two step cosmetic composition according to the invention is used as a lipstick, a lipgloss or a lipgel. The cosmetic composition according to the invention can be formulated as a normal fatty stick showing a high brilliance and a high opacity. Due to the resulting elastomeric films the lipsticks are further are resistant to transferring colors to objects which come into direct contact with the lips, such as glasses, cups, clothings, fingers and the like. Further the resulting elastomeric films are highly flexible which contribute to their long-wearing properties, decreased cracking and increased comfort. Lipsticks according to the invention show a clearly volumetric effect, are resistant to hydrophilic and lipophilic solvents and highly comfortable to the wearer.

For a lipstick according to the invention at least a wax with a high melting point, preferably with a melting point higher than 50° C., colorants, mineral particles and optionally preservatives and a solvent are mixed together with the reactants of the first part of the cosmetic composition. In a preferred embodiment the siloxane polymer and/or the polyol and the hydrosiloxane are contained in the first part of a lipstick according to the invention. The appropriate second part of the two-part lipstick comprises the catalyst and a solvent.

A lipgloss according to the invention comprises in the first part of the cosmetic composition two of the reactants and at least a wax with a low melting point, preferably with a melting point less than 50° C. and/or polyethylene, colorants, mineral particles and optionally preservatives and a solvent. Preferably the siloxane polymer and/or a polyol and the catalyst are combined in the first part of the composition. The appropriate second part of the composition consists of the hydrosiloxane and a solvent.

A lipgel according to the invention comprises in the first part of the cosmetic composition two of the reactants and at least colorants and optionally preservatives and a solvent. Preferably the siloxane polymer and/or a polyol and the hydrosiloxane are combined in the first part of the composition. The appropriate second part of the composition consists of the catalyst and a solvent.

In a further object of the invention the two-part cosmetic composition is applied subsequently to a biological surface, preferably to human skin. In a preferred embodiment the part which contains most of the ingredients is applied first. If one part of the composition is a solid, it is advantageous to apply this part of the composition first. If both parts of the compositions are liquids, preferably the part with the higher viscosity is applied first. In another preferred embodiment the siloxane polymer containing part is applied first to the human skin. As soon as the other part of the composition is applied over the first one the dehydrogenative coupling is introduced which effects both the hydrogen generation comprising the foaming and the curing of the silicone polymer which results in the swelling effect. Alternatively, both parts of the composition can be mixed immediately before the application and applied together in a single step, but the separate application of the two parts is preferred.

It is also advantageous for the consumers that the colorant, if any, is contained in the first part of the composition. So the colour coating can be applied to consumers satisfaction without inducing the dehydrogenative coupling.

It is a further object of the invention to use the two part cosmetic composition as lipstick, lipgloss, lipgel, mascara, foundation or face makeup.

In another preferred embodiment the two-part cosmetic composition can also be applied to other biological substrates to which a swelling effect is desired, such as hairs, eyelashes or eyebrows.

It is a further object of the invention to provide a kit comprising in different chambers of a single two chambered container or in two separate containers the two part cosmetic composition.

The following examples are offered to illustrate the two-part cosmetic product of the present invention. They are not intended to be limiting in any respect.

EXAMPLE 1

A two-part lipgloss composition is prepared which contains in one part, preferably the first part of the composition:
25 weight % Dimethiconol in Cyclomethicone
10 weight % Polyethylene
10 weight % Colorants (Iron oxides, Red 7 Ca. Lake)
10 weight % Mica
43 weight % Cyclomethicone
1 weight % Caprylyl Glycol
1 weight % Platinum-divinyl tetramethyldisiloxane The weight % are based on the total weight of the first part of the two-part lipgloss composition.

The first part of the composition is prepared by heating the dimethiconol in cyclomethicone, the polyethylene and the preservative (caprylyl glycol) up to 50° C. and mixing them until they are homogeneous. While the mixture is stirred the mica, the colorant(s), and the platinum-divinyl tetramethyldisiloxane are added together with the cyclomethicone. In order to maintain the catalytic activity the mixture may not be heated over 50° C. Then the mixture is cooled down to room temperature under continuous stirring.

The second part of the two-part lipgloss composition comprises 15 weight polymethylhydrosiloxane solved in 85 weight % cyclomethicone based on the total weight of the second part of the two-part lipgloss composition.

EXAMPLE 2

A two-part lipstick composition is prepared which contains in one part, preferably the first part of the composition:
25 weight % Dimethiconol in Cyclomethicone
20 weight % PEG8-Beeswax
10 weight % Colorant(s) (Red 7 Ca. Lake)
5 weight % Mica
24 weight % Cyclomethicone
1 weight % Caprylyl Glycol
15 weight % Polymethylhydrosiloxane The weight % are based on the total weight of the first part of the two-part lipstick composition.

The first part of the composition is prepared by heating the dimethiconol in cyclomethicone, the PEG8-Beeswax and the preservative up to 80° C. and mixing them until they are homogeneous. While the mixture is stirred the mica, the colorant(s) and the polymethylhydrosiloxane are added together with the cyclomethicone. Then the mixture is cooled down to room temperature under continuous stirring.

The second part of the two-part lipstick composition comprises 1 weight % platinum-divinyl tetramethyldisiloxane and 99 weight % cyclomethicone based on the total weight of the second part of the two-part lipstick composition.

EXAMPLE 3

A two-part lipgel composition is prepared which contains in one part, preferably the first part of the composition:
20 weight % Iron oxides and Red 7 Ca. Lake
2 weight % Caprylyl Glycol
78 weight % Cyclomethicone The weight % are based on the total weight of the first part of the two-part lipgel composition. Iron oxides and Red 7 Ca. Lake are treated with dimethiconol copolymer blended with polymethylhydrosiloxane. The treated pigments are mixed with the preservatives and the cyclomethicone until they are homogeneous.

The second part of the two-part lipgel composition comprises 1 weight % platinum-divinyl tetramethyldisiloxane and 99 weight % cyclomethicone based on the total weight of the second composition.

EXAMPLE 4

A two-part lipstick composition is prepared which contains in one part, preferably the first part of the composition:
45 weight % castor oil
8 weight % Risocast DA-H
15 weight % PEG8-Beeswax 15 weight % Colorant(s) (Red 7 Ca. Lake)
10 weight % Esters
5 weight % Mica
1 weight % Caprylyl Glycol
1 weight % Polydimethylhydrosiloxane The weight % are based on the total weight of the first part of the two-part lipstick composition.

The first part of the composition is prepared by heating the hydrogenated castor oil dimer dilinoleate, the PEG8-Beeswax and the preservative up to 80° C. and mixing them until they are homogeneous. While the mixture is stirred the mica, the colorant(s) and the polymethylhydrosiloxane are added. Then the mixture is cooled down to room temperature under continuous stirring.

The second part of the two-part lipstick composition comprises 1 weight platinum-divinyl tetramethyldisiloxane and 99 weight % cyclomethicone based on the total weight of the second part of the two-part lipstick composition.

EXAMPLE 5

A two-part lipgloss composition is prepared which contains in one part, preferably the first part of the composition:
25 weight % Dimethiconol in Cyclomethicone
25 weight % Risocast DA-H
10 weight % Polyethylene
10 weight % Colorants (Iron oxides, Red 7 Ca. Lake)
10 weight % Mica
18 weight % Cyclomethicone
1 weight % Caprylyl Glycol
1 weight % Platinum-divinyl tetramethyldisiloxane The weight % are based on the total weight of the first part of the two-part lipgloss composition.

The first part of the composition is prepared by mixing the dimethiconol in cyclomethicone and the hydrogenated castor oil dimer dilinoleate. The resulting mixture is heated together with the polyethylene and the preservative (caprylyl glycol) up to 50° C. and mixed them until a homogeneous mixture is achieved. While stirring the mica, the colorant(s), and the platinum-divinyl tetramethyl-disiloxane are added together with the cyclomethicone. In order to maintain the catalytic activity the mixture may not be heated over 50° C. Then the mixture is cooled down to room temperature under continuous stirring.

The second part of the two-part lipgloss composition comprises 15 weight polymethylhydrosiloxane solved in 85 weight % cyclomethicone based on the total weight of the second part of the two-part lipgloss composition.

The invention claimed is:

1. A two-part cosmetic composition for providing an expanded elastomeric transfer resistant film on a biological surface to impart a swelling effect, the two-part cosmetic composition comprising:
   one or more siloxane polymers;
   a hydrosiloxane with at least two Si—H units; and
   a catalyst,
   wherein, with the exception of the hydrosiloxane, all of the siloxane polymers present in the two-part cosmetic composition have at least two hydroxy-functionalized terminal groups,
   wherein the hydrosiloxane and the catalyst are separate from each other in a first part and a second part of the cosmetic composition,
   wherein the one or more siloxane polymers are contained in an amount of 1 to 60 percent by weight, based on total weight of the siloxane polymer containing part,
   wherein the catalyst is contained in an amount of 0.001 to 3 percent by weight based on total weight of the catalyst containing part,
   wherein the hydrosiloxane is contained in an amount of 0.1 to 50 percent by weight based on total weight of the hydrosiloxane containing part and comprises at least dimethiconol;
   wherein the catalyst catalyzes, in-situ, a dehyrogenative coupling reaction that, upon combining the first part and the second part, crosslinks at least one component of the two-part cosmetic composition and the hydrosiloxane to form the expanded elastomeric transfer resistant film; and
   wherein the composition further comprises hydrogenated caster oil dimer dilinoleate.

2. The two part cosmetic composition of claim 1, wherein the one or more siloxane polymers further comprises a dimethiconol copolymer, or a hydroxyl-functionalized derivative thereof and/or a hydroxy-functional silicate resin, or a mixture thereof.

3. The two part cosmetic composition of claim 1, wherein the one or more siloxane polymers further comprises a dimethiconol silicone silicate copolymer.

4. The two part cosmetic composition of claim 1, wherein the hydrosiloxane is polymethyl hydrosiloxane.

5. The two part cosmetic composition of claim 1, wherein the catalyst comprises a metal selected from the transition metals of the VIII B group of the chemistry's periodic table.

6. The two part cosmetic composition of claim 1, wherein the cosmetic composition comprises cosmetically acceptable auxiliary substances.

7. The two part cosmetic composition of claim 1, being a solid, a pressed powder, a creme, a gel, a lotion or a liquid.

8. A kit comprising in different chambers of a single two chambered container or in two separate containers the two part cosmetic composition of claim 1.

9. A method for applying the two part cosmetic composition of claim 1 to a biological surface, wherein one part of the cosmetic composition is applied first and the other part is applied subsequently or wherein both parts are mixed immediately before the application and applied together in a single step.

10. The method according to claim 9, wherein said cosmetic composition is selected from the group consisting of a lipstick, a lipgloss, a lipgel, a mascara, a foundation, and a face makeup.

11. The two part cosmetic composition of claim 1, wherein the one or more siloxane polymers further comprises a silicone silicate copolymer.

12. The two part cosmetic composition of claim 1, wherein the one or more siloxane polymers further comprises trimethylsiloxysilicate.

13. The two part cosmetic composition of claim 1, wherein the catalyst comprises a platinum-divinyl tetramethyldisiloxane complex.

14. The two part cosmetic composition of claim 1, wherein the hydrosiloxane is contained in an amount of 10 to 25% percent by weight based on total weight of the hydrosiloxane containing part.

* * * * *

UNITED STATES PATENT AND TRADEMARK OFFICE
CERTIFICATE OF CORRECTION

PATENT NO. : 9,445,984 B2  
APPLICATION NO. : 12/866971  
DATED : September 20, 2016  
INVENTOR(S) : Mateu et al.

Page 1 of 1

It is certified that error appears in the above-identified patent and that said Letters Patent is hereby corrected as shown below:

On the Title Page

In item (30), in "Foreign Application Priority Data", in Column 1, Line 1, delete "08151337" and insert --08151337.6--, therefor In item (30), in "Foreign Application Priority Data", in Column 1, Line 2, delete "08162917" and insert --08162917.2--, therefor In item (57), in "Abstract", in Column 2, Line 7, delete "siloxan" and insert --siloxane--, therefor Signed and Sealed this  
Thirteenth Day of March, 2018

Andrei Iancu  
*Director of the United States Patent and Trademark Office*